United States Patent
Ryu et al.

(10) Patent No.: US 9,725,374 B2
(45) Date of Patent: Aug. 8, 2017

(54) SYSTEM AND METHOD FOR PREVENTING CATALYST FROM OVERHEATING

(71) Applicant: Korea Institute of Energy Research, Daejeon (KR)

(72) Inventors: Ho-jung Ryu, Daejeon (KR); Dong-ho Lee, Daejeon (KR); Gyoung-tae Jin, Daejeon (KR); Do-won Shun, Daejeon (KR); Chang-keun Yi, Daejeon (KR); Jae-hyeon Park, Daejeon (KR); Dal-hee Bae, Sejong (KR); Sung-ho Jo, Daejeon (KR); Seung-yong Lee, Daejeon (KR); YoungCheol Park, Daejeon (KR); Jong-ho Moon, Seoul (KR); Ji-bong Joo, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 194 days.

(21) Appl. No.: 14/540,856

(22) Filed: Nov. 13, 2014

(65) Prior Publication Data
US 2016/0046540 A1    Feb. 18, 2016

(30) Foreign Application Priority Data
Aug. 18, 2014    (KR) .................. 10-2014-0106982

(51) Int. Cl.
*C10L 3/08*    (2006.01)
*B01J 8/12*    (2006.01)
(Continued)

(52) U.S. Cl.
CPC .............. *C07C 1/042* (2013.01); *B01J 8/005* (2013.01); *B01J 8/0015* (2013.01); *B01J 8/0055* (2013.01);
(Continued)

(58) Field of Classification Search
CPC . B01J 8/1836; B01J 8/12; B01J 8/1818; B01J 8/28; B01J 8/388; B01J 2208/00132
See application file for complete search history.

(56) References Cited

U.S. PATENT DOCUMENTS 2,474,583 A  *  6/1949  Lewis, Jr. ............... C07C 1/048
                                                    208/159
2,573,795 A  *  11/1951  Lanning ..................... B01J 8/24
                                                    518/706
(Continued)

FOREIGN PATENT DOCUMENTS

KR    10-1991-0001346    1/1991    ............... F28D 7/00
KR    10-2011-0143946    12/2011    ............... B01J 8/02
(Continued)

OTHER PUBLICATIONS

Office Action dated Sep. 22, 2015, in the Korean Patent Office with partial English language translation.

*Primary Examiner* — Matthew Merkling
(74) *Attorney, Agent, or Firm* — Harness, Dickey & Pierce, P.L.C.

(57) ABSTRACT

A system for preventing a catalyst from overheating is provided. The system includes: a first reactor filled with a catalyst at least in part and configured to receive reaction gas and produce product gas; and a second reactor configured to cool a catalyst discharged from the first reactor. The catalyst is circulated between the first reactor and the second reactor by injecting the catalyst cooled in the second reactor into the first rector.

4 Claims, 3 Drawing Sheets

(51) Int. Cl.
    *B01J 8/28*     (2006.01)
    *B01J 8/26*     (2006.01)
    *C07C 1/04*     (2006.01)
    *B01J 8/18*     (2006.01)
    *B01J 8/38*     (2006.01)
    *B01J 8/00*     (2006.01)

(52) U.S. Cl.
    CPC ............... *B01J 8/12* (2013.01); *B01J 8/1809* (2013.01); *B01J 8/1818* (2013.01); *B01J 8/1827* (2013.01); *B01J 8/1836* (2013.01); *B01J 8/1872* (2013.01); *B01J 8/26* (2013.01); *B01J 8/28* (2013.01); *B01J 8/388* (2013.01); *C07C 1/045* (2013.01); *C07C 1/049* (2013.01); *C07C 1/0415* (2013.01); *C10L 3/08* (2013.01); *B01J 8/1863* (2013.01); *B01J 2208/0053* (2013.01); *B01J 2208/00132* (2013.01); *B01J 2208/00752* (2013.01); *B01J 2208/00761* (2013.01); *C10L 2290/06* (2013.01); *C10L 2290/10* (2013.01); *C10L 2290/12* (2013.01); *C10L 2290/42* (2013.01)

(56) References Cited

U.S. PATENT DOCUMENTS

| | | | | |
|---|---|---|---|---|
| 2,622,970 | A | * | 12/1952 | Martin ................... B01J 8/1836 208/163 |
| 2,775,512 | A | * | 12/1956 | Leithauser ............ C07C 1/0415 422/200 |
| 4,433,066 | A | * | 2/1984 | Hackler ................... B01J 8/006 48/127.7 |
| 5,120,691 | A | | 6/1992 | Pontier et al. ................... 502/44 |
| 2011/0035990 | A1 | * | 2/2011 | Kammerloher .......... C10G 2/32 44/311 |
| 2013/0210938 | A1 | | 8/2013 | Eastland et al. .......... C10L 3/08 |

FOREIGN PATENT DOCUMENTS

| | | | |
|---|---|---|---|
| KR | 10-2012-0153853 | 12/2012 | ............... C07C 9/04 |
| KR | 10-2013-0075549 | 7/2013 | ............... B01J 8/02 |
| KR | 10-2013-0095647 | 8/2013 | ............... C10L 3/08 |
| KR | 10-2014-0084486 | 7/2014 | ............... C07C 9/04 |

\* cited by examiner

SYSTEM AND METHOD FOR PREVENTING CATALYST FROM OVERHEATING

CROSS-REFERENCE TO RELATED PATENT APPLICATION

This application claims priority from Korean Patent Application No. 2014-0106982, filed on Aug. 18, 2014 in the Korean Intellectual Property Office, the disclosure of which is incorporated herein by reference in its entirety.

FIELD

Apparatuses and methods consistent with the exemplary embodiments relate to a system and method for preventing a catalyst from overheating, and more particularly, to a system and method for preventing a catalyst from overheating, which is appropriate for a chemical reaction which uses a catalyst and is accompanied by heat of reaction.

BACKGROUND

Technology for utilization of coal which is cheap and abundant is being widely developed due to the price rise of crude oil and natural gas. In particular, Synthetic Natural Gas (SNG) technology is methods for producing fuel gas which includes methane as a main component by using a solid fuel such as coal, etc., and is satisfactory from the aspects of energy security and environmental issue of use of energy. In addition, the SNG technology can use a natural gas infrastructure as it is and thus may be the most realistic clean coal technology along with technology of Integrated Gasification Combined Cycle (IGCC).

From among the methods for producing SNG, an indirect method for obtaining SNG from syngas obtained by gasifying coal through a methane synthesis reaction using a catalyst is widely used. This method goes through a production process shown in FIG. 1, for example.

Referring to FIG. 1, first, syngas including carbon monoxide (CO) and hydrogen ($H_2$) as main components is obtained by gasifying coal in a coal gasifier 1. Since a $H_2$/CO ratio of the syngas discharged from the coal gasifier is below 1.0, a water gas shift reaction is performed in a water gas shift reactor 2 to increase a $H_2$ concentration to make the $H_2$/CO ratio reach about 3.0. This reaction is an exothermic reaction and has difficulty in controlling heat of reaction. Therefore, when temperature of a catalyst excessively increases, original activation is lost and a water gas shift reaction may not occur. In this case, it is common that the $H_2$/CO ratio is adjusted to be about 3.0 by passing only 30% of the syngas through the water gas shift reactor and bypassing the remaining syngas.

The syngas which has gone through the coal gasification and water gas shift reaction is cooled in a cooling device 3, sulfide (e.g., $H_2S$, COS) and carbon dioxide ($CO_2$) are removed in a desulfurization/$CO_2$ separating device 4, and then the syngas is introduced to a methanation reactor 5.

In the methanation reactor 5, methane is synthesized by a reaction of CO and $H_2$. The methane synthesis reaction is a strong exothermic reaction and high pressure condition is favorable thermodynamically. However, as reaction temperature increases, a methane yield is reduced. Therefore, extracting and controlling heat of reaction effectively to obtain a high methane yield are the most important factor in designing a methanation reactor.

For example, Korean Patent Publication No. 2013-0095647 discloses controlling such heat of reaction. This disclosure suggests a method which uses a plurality of reactors in a methane synthesis process, and controls heat of reaction by re-circulating products discharged from some reactors to the former reactor, mixing the products with newly introduced gas, and reducing concentrations of CO and $H_2$ of supplied gases. In this method, however, a methane composition of 90% or more can be obtained only if at least 3-stage or 4-stage reactors are used, and there is a problem that many reactors, a heat exchanger, and a gas re-circulation system are required to control heat of methanation reaction.

In addition, Korean Patent Publication Nos. 2013-0075549 and 2014-0084486 propose a method using a reactor which has a heat exchanger installed inside or outside a catalyst layer. However, this method has disadvantages that a structure is complicated and it is difficult to replace a catalyst when activation of a catalyst is degraded. In addition, since most of the methanation catalysts is manufactured in the form of a tablet or pallet, the methanation catalyst is used in a fixed bed type reactor, and heat generated by the reaction is stored from the starting region when syngas is supplied to the fixed bed reactor. Therefore, there is a problem that temperature is not uniformly distributed over the reactor.

SUMMARY

One or more aspects of the exemplary embodiments provide a system for preventing a catalyst from overheating, which simply includes a first reactor and a second reactor and can produce product gas from reaction gas and simultaneously perform catalyst heat exchange.

One or more aspects of the exemplary embodiments also provide a system for preventing a catalyst from overheating, which includes a first reactor and a second reactor of a fluidized bed type, thereby achieving high heat and mass transfer, a high methane yield, and a high heat control effect in comparison with a related art fixed bed type reactor.

One or more aspects of the exemplary embodiments also provide a system for preventing a catalyst from overheating, which includes a first reactor and a second reactor of a fluidized bed type, thereby facilitating recovering and replenishing of a catalyst and making temperature distribution uniform in the reactor by mixing catalyst particles by fluidization.

According to an aspect of an exemplary embodiment, there is provided a system for preventing a catalyst from overheating, the system including: a first reactor filled with a catalyst at least in part and configured to receive reaction gas and produce product gas; and a second reactor configured to cool a catalyst discharged from the first reactor, wherein the catalyst is circulated between the first reactor and the second reactor by injecting the catalyst cooled in the second reactor into the first rector.

According to an aspect of another exemplary embodiment, there is provided a method for preventing a catalyst from overheating, the method including: producing product gas by supplying reaction gas to a first reactor filled with a catalyst at least in part; and discharging some of the catalyst from the first reactor and supplying the catalyst to a second reactor; cooling the catalyst in the second reactor; and supplying the catalyst cooled in the second reactor to the first reactor.

According to one or more exemplary embodiments, since the first reactor to produce product gas from reaction gas and the second reactor to exchange heat with a catalyst are simply used, the system can produce product gas and simultaneously control an amount of heat of the catalyst with a simple configuration.

According to one or more exemplary embodiments, since the first reactor and the second reactor of the system may be fluidized bed type reactors, high heat and material transfer, a high methane yield, and a high heat control effect can be achieved in comparison with a related art of fixed bed type reactor.

According to one or more exemplary embodiments, since the first reactor and the second reactor of the system may be fluidized bed type reactors, it is easy to recover and replenish a catalyst in comparison with a related-art fixed bed reactor and it is easy to make temperature distribution uniform in the reactor by mixing catalyst particles by fluidization.

Additional aspects and advantages of the exemplary embodiments will be set forth in the detailed description, will be obvious from the detailed description, or may be learned by practicing the exemplary embodiments.

BRIEF DESCRIPTION OF THE DRAWINGS

The above and other features and advantages will become more apparent by describing in detail exemplary embodiments with reference to the attached drawings in which.

DETAILED DESCRIPTION

Figure 1:
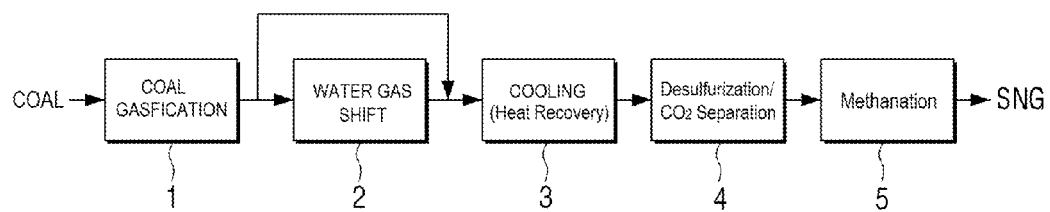
FIG. 1 is a view to illustrate an exemplary production process for producing SNG.

Exemplary embodiments will now be described more fully with reference to the accompanying drawings to clarify aspects, features and advantages of the inventive concept. The exemplary embodiments may, however, be embodied in many different forms and should not be construed as limited to the exemplary embodiments set forth herein. Rather, the exemplary embodiments are provided so that this disclosure will be thorough and complete, and will fully convey the scope of the application to those of ordinary skill in the art.

It will be understood that when an element is referred to as being "on" (or "under", "on the right of", or "on the left of") another element, the element can be directly on (or "under", "on the right of", or "on the left of") another element or intervening elements. In the drawings, thicknesses of elements are exaggerated for easy understanding of technical features.

The expressions such as "upper (top)", "lower (bottom)", "left", "right", "front", "rear", etc. used in the specification to explain a location relationship between elements do not mean a directions or location as an absolute criterion and are relative expressions used for convenience of explanation with reference to a corresponding drawing when the present invention is explained with reference to each drawing.

If the terms such as 'first' and 'second' are used to describe elements, these element should not be limited by such terms. These terms are used for the purpose of distinguishing one element from another element only. The exemplary embodiments include their complementary embodiments.

The terms used herein are for the purpose of describing particular exemplary embodiments only and are not intended to be limiting. As used herein, the singular forms "a", "an" and "the" are intended to include the plural forms as well, unless the context clearly indicates otherwise. It will be further understood that the terms "comprises" and/or "comprising," when used in this specification, do not preclude the presence or addition of one or more other components.

Hereinafter, exemplary embodiments will be described in greater detail with reference to the accompanying drawings. The matters defined in the description, such as detailed construction and elements, are provided to assist in a comprehensive understanding of the exemplary embodiments. However, it is apparent that the exemplary embodiments can be carried out by those of ordinary skill in the art without those specifically defined matters. In the description of the exemplary embodiment, certain detailed explanations of related art are omitted when it is deemed that they may unnecessarily obscure the essence of the inventive concept.

A system for preventing a catalyst from overheating according to an exemplary embodiment includes a process of producing product gas from reaction gas by using a catalyst and a process of cooling the catalyst. In this case, the reaction gas, the product gas, and the catalyst used in the system for preventing a catalyst from overheating may vary according to an exemplary embodiment.

Hereinafter, the system for preventing a catalyst from overheating is used as a methanation reactor for generating SNG from syngas by way of an example. That is, in this example, the reaction gas is syngas including hydrogen and carbon monoxide as main components, and the SNG includes methane as a main component. However, the system for preventing a catalyst from overheating is not limited to use as the methanation reactor and may be used as a reactor for a certain reaction process accompanied by heat such as a water gas shift reaction and etc.

Figure 2:
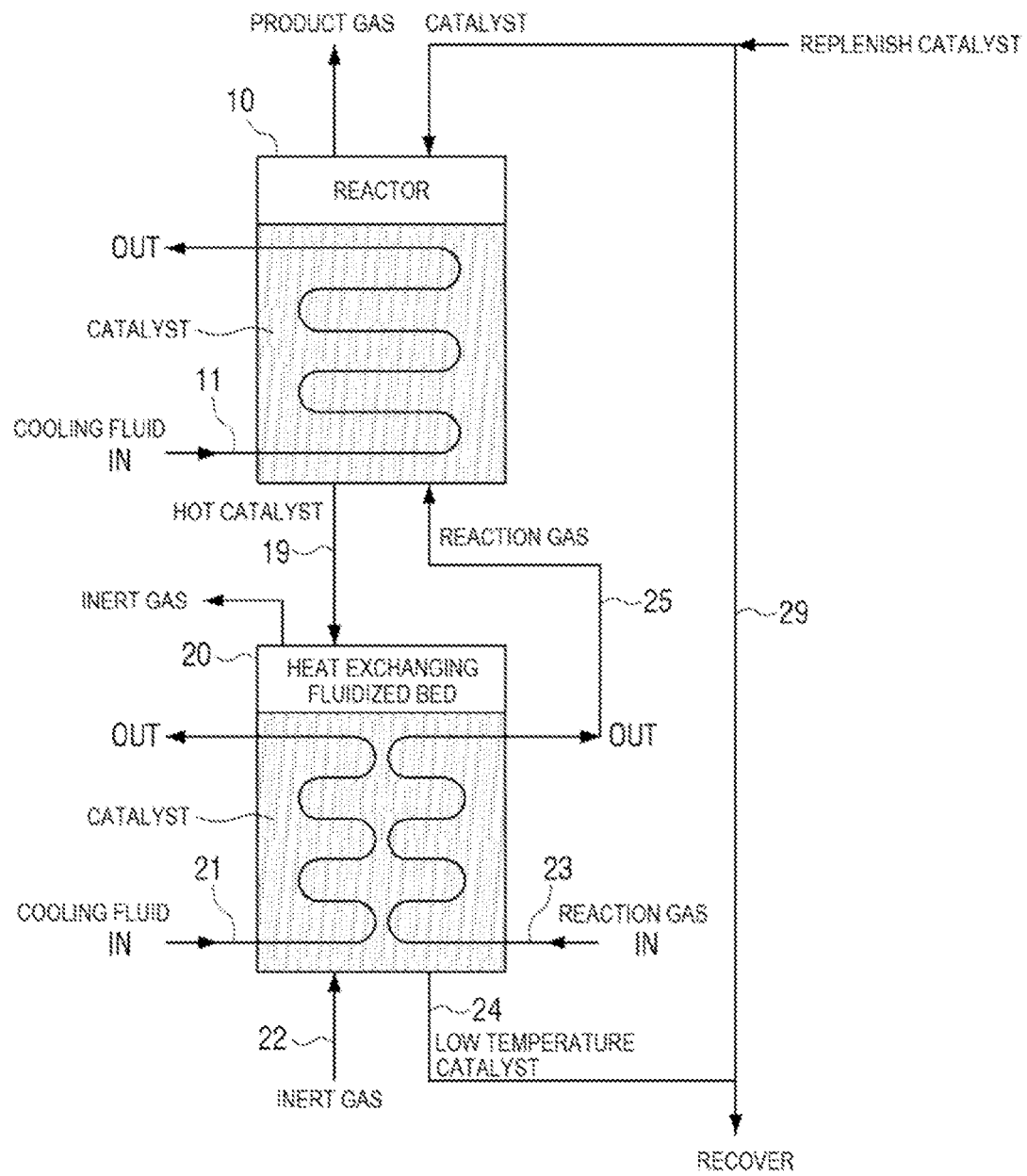
FIG. 2 is a schematic view of a system for preventing a catalyst from overheating according to an exemplary embodiment.

FIG. 2 is a schematic view of a system for preventing a catalyst from overheating according to an exemplary embodiment.

Referring to FIG. 2, the system for preventing a catalyst from overheating according to an exemplary embodiment includes a first reactor 10 and a second reactor 20. In the exemplary embodiment in which the system for preventing a catalyst from overheating is used as a methanation reactor, the first reactor 10 is a methanation reactor and the second reactor 20 is a heat exchanging reactor to cool a catalyst.

The first reactor 10 is filled with a catalyst at least in part and receives reaction gas and produces product gas. In this case, the reaction gas is syngas containing hydrogen and carbon monoxide and the product gas is SNG containing methane.

In an exemplary embodiment, the catalyst is a general catalyst used in a methane synthesis reaction. For example, a nickel-based catalyst, that is, a nickel-based catalyst containing $Al_2O_3$, may be used, but is not limited to this. According to an exemplary embodiment, the catalyst may be a particle shape catalyst having a diameter ranging from 1 to 9,000 micrometers.

The catalyst in the first reactor 10 may exist in the form of a fluidized bed. That Is, the reaction gas (that is, syngas) injected through a reaction gas inflow pipe 25 functions as a fluidizing gas and accordingly the catalyst particles in the first reactor 10 are fluidized. To achieve this, a gas flow velocity of the reaction gas injected into the first reactor 10 should be greater than or equal to a minimum fluidization velocity of the catalyst particles.

The fluidized catalyst particles show characteristics of fluids and the catalysts can be smoothly mixed and temperature distribution in the fluidized bed is uniform in comparison with in a fixed bed using catalysts of a tablet or pellet form, so that a heat and mass transfer rate is very high.

The first reactor 10 may include a path 11 of a first cooling fluid passing through the first reactor 10. Accordingly, heat generated by the methanation reaction of the syngas can be cooled by the first cooling fluid. The first cooling fluid may be one of the fluids such as water, boiler water, cooling oil, antifreezing solution, etc. but is not limited to these. The first cooling fluid is heated while passing through the first reactor 10 along the path 11 and heat energy of the heated first cooling fluid may be recovered through a certain device (not shown).

The hot catalyst which has gone through the methanation reaction in the first reactor 10 is transferred to the second reactor 20 through a discharge pipe 19 connecting the first reactor 10 and the second reactor 20.

The second reactor 20 is filled with the catalyst received from the first reactor 10 at least in part and functions as a heat exchanging reactor to cool the catalyst.

According to an exemplary embodiment, the second reactor 20 is a heat exchanging fluidized bed reactor in which a catalyst exists in the form of a fluidized bed. In this case, fluidization of the heat exchanging fluidized bed is performed by a fluidizing gas supplied from a lower portion of the second reactor 20 through a fluidizing gas inflow pipe 22. The fluidizing gas may be an inert gas and/or steam. When steam is used, the steam absorbs heat of the catalyst, thereby reducing heat of the catalyst, and hot steam is discharged from the second reactor 20.

The second reactor 20 may include a path 21 of a second cooling fluid to cool the catalyst filled in the second reactor 20. The second cooling fluid may be one of the fluids such as water, boiler water, cooling oil, antifreezing solution, etc., but is not limited to these. When the second cooling fluid exchanges heat with the catalyst and is heated when passing through the second reactor 20 along the path 21, and heat energy of the heated second cooling fluid may be recovered through a certain device (not shown). According to an exemplary embodiment, the first cooling fluid and the second cooling fluid are the same fluid and may be supplied from a same cooling fluid storage tank through the first cooling fluid path 11 and the second cooling fluid path 21.

According to an exemplary embodiment, the second reactor 20 may further include a reaction gas path 23 to pre-heat the reaction gas to be injected into the first reactor 10. The reaction gas path 23 is connected to the reaction gas inflow pipe 25 of the first reactor 10. When the reaction gas passes through the second reactor 20 along the reaction gas path 23, the reaction gas exchanges heat with the catalyst in the second reactor 20 and is pre-heated to a methanation reaction temperature, and then is injected into the first reactor 10.

Although the second reactor 20 includes both the second cooling fluid path 21 and the reaction gas path 23 to achieve heat exchange with the catalyst in the illustrated exemplary embodiment, the second reactor 20 may include only one of the second cooling fluid path 21 and the reaction gas path 23 in an alternative exemplary embodiment.

The catalyst cooled by the heat exchanging with the second cooling fluid and/or the reaction gas is re-circulated into the first reactor 10. The catalyst is discharged from the second reactor 20 through a discharge pipe 24 and is injected back into the first reactor 10 along a re-circulation path 29. During this process, some catalyst may be recovered as a spent catalyst and a new catalyst is replenished.

According to the above-described exemplary embodiment, by using only the first reactor for producing the product gas from the reaction gas and the second reactor for exchanging heat with the catalyst, the product gas can be produced and heat of the catalyst can be controlled. In addition, since the first reactor 10 and the second reactor 20 may be fluidized bed reactors, heat and mass transfer is high in comparison with that of a related art fixed bed reactor and thus a high methane yield and a high heat control effect can be achieved. In addition, the related-art fixed bed reactor has difficulty in recovering and replenishing the catalyst continuously, whereas the fluidized bed reactor in the exemplary embodiment has a simple configuration and catalyst particles are re-circulated, and thus it is easy to recover and replenish the catalyst.

Figure 3:
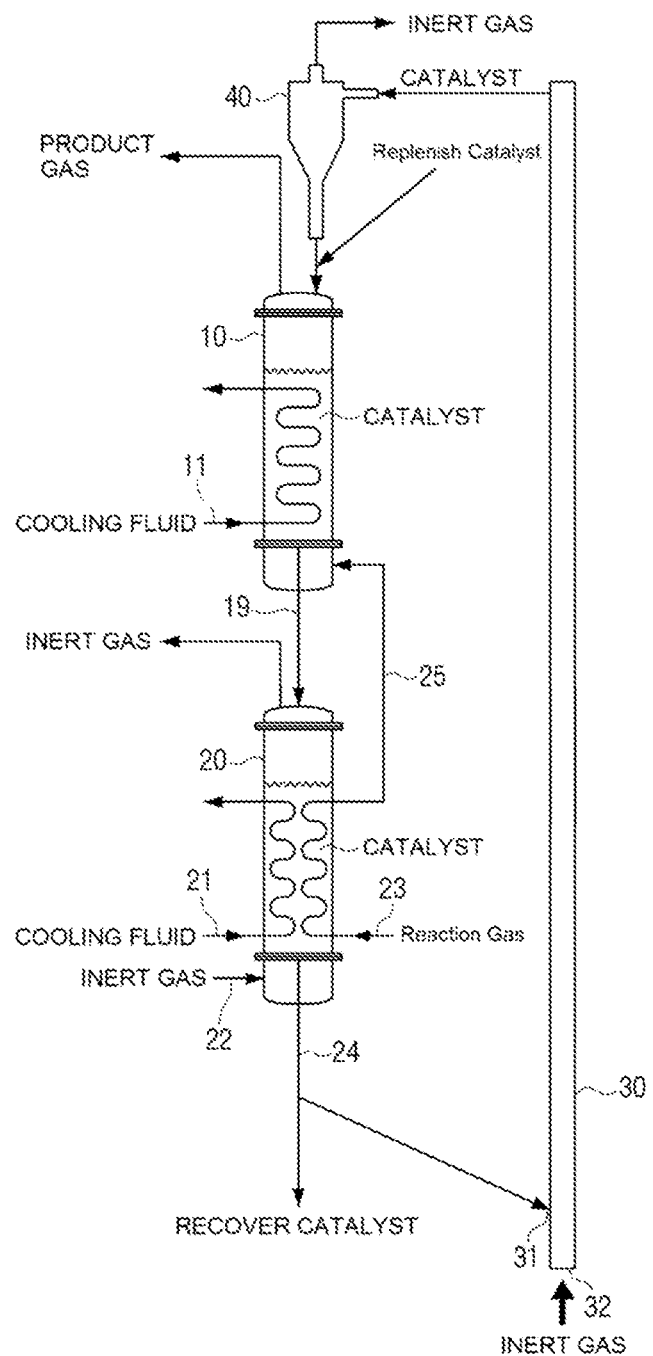
FIG. 3 is a view illustrating a configuration of a system for preventing a catalyst from overheating according to an exemplary embodiment.

FIG. 3 is a view illustrating an example of a configuration of a system for preventing a catalyst from overheating according to an exemplary embodiment, and illustrates the system of FIG. 2 in detail.

Referring to FIG. 3, the system for preventing a catalyst from overheating according to an exemplary embodiment includes a first reactor 10, a second reactor 20, a riser tube 30, and a cyclone 40. The first reactor 10 and the second rector 20 are the same as or similar to the first reactor and the second reactor described above with reference to FIG. 2, and thus a detailed description thereof is omitted.

The system for preventing a catalyst from overheating according to the illustrated exemplary embodiment is used for a methane synthesis reaction, and accordingly, the first reactor 10 is a methanation reactor and the second reactor 20 operates as a heat exchanging reactor to cool a catalyst.

In addition, a reaction gas injected into the first reactor 10 is syngas containing carbon monoxide and hydrogen, and a product gas generated in the first reactor 10 is SNG including methane as a main component. The catalyst may be a general catalyst used in a methane synthesis reaction like a nickel-based catalyst.

In an alternative exemplary embodiment, the system for preventing a catalyst from overheating of FIG. 3 may be used for a different chemical reaction other than the methane synthesis reaction. In this case, components of the reaction gas, product gas, and the catalyst may be different.

In the illustrated exemplary embodiment, the first reactor 10 is a fluidized bed reactor and is filled with a methanation catalyst. The catalyst may be a catalyst of a particle type having a diameter ranging from 1 to 9,000 micrometers.

The reaction gas is supplied to the first reactor 10 through a reaction gas inflow pipe 25. A gas velocity (U) of the reaction gas is kept greater than or equal to a minimum fluidization velocity (Umf) of the catalyst particles to fluidize the methanation catalyst, and is kept lower than a terminal velocity (Ut) of the catalyst particles to minimize loss caused by entrainment or elutriation of catalysts. That is, the gas velocity of the reaction gas may satisfy Umf≤U<Ut.

The first reactor 10 includes a first cooling fluid path 11 to allow a first cooling fluid to pass through the first reactor 10. The catalyst heated by a reaction of the reaction gas in the first reactor 10 is cooled by the first cooling fluid and the first cooling fluid is discharged along the path 11 after being heated.

The catalyst heated in the first reactor 10 is conveyed to the second reactor 20 through a discharge pipe 19 (by gravity, for example). In the illustrated exemplary embodiment, the second reactor 20 is a fluidized bed reactor and is filled with the catalyst received from the first reactor 10.

A fluidizing gas flows in from a lower portion of the second reactor 20 through a fluidizing gas inflow pipe 22. The fluidizing gas may be an inert gas and a velocity of the fluidizing gas is higher than or equal to the minimum fluidization velocity of the catalyst and is lower than the terminal velocity similarly to that of the first reactor 10.

In the illustrated exemplary embodiment, the second reactor 20 includes a second cooling fluid path 21 and a reaction gas path 23 passing through the second reactor 20. Accordingly, the catalyst in the second reactor is more cooled by the second cooling fluid and the reaction gas, and the cooled catalyst is discharged from the second reactor 20 through a discharge pipe 24 (by gravity, for example).

In an alternative exemplary embodiment, the second reactor 20 may include only one of the second cooling fluid path 21 and the reaction gas path 23. In addition, the second cooling fluid may be the same as the first cooling fluid or a different fluid. The reaction gas pre-heated by passing through the second reactor 20 along the reaction gas path 23 is injected into the first reactor 10 through the reaction gas inflow pipe 25 of the first reactor 10.

Some of the catalyst discharged from the second reactor 20 may be recovered and the remaining catalyst is conveyed along a re-circulation path (29 of FIG. 2). The re-circulation path 29 of FIG. 2 may be implemented by using the riser tube 30 and the cyclone 40 in the exemplary embodiment of FIG. 3. In this exemplary embodiment, the catalyst discharged from the second reactor 20 is conveyed to the riser tube 30. The riser tube 30 may have a shape of an empty polygon or cylinder, and includes a first inflow pipe 31 to receive the catalyst from the second reactor 20 and a second inflow pipe 32 to receive gas to form an ascending current under the first inflow pipe 31.

In the illustrated exemplary embodiment, an inert gas flows into the second inflow pipe 32 of the riser tube 30 and forms an ascending current in the riser tube 30. In this case, when an inert gas having temperature lower than that of the catalyst is used, the catalyst can be additionally cooled in the riser tube 30. In addition, a flow velocity in the riser tube 30 is kept higher than a transport velocity (Utr) of the catalyst, so that all of the catalysts flowing in through the first inflow pipe 31 are conveyed to an upper portion of the riser tube 30.

The catalyst particles conveyed to the upper portion of the riser tube 30 by the inert gas flows into the cyclone 40 along with the inert gas. The cyclone 40 separates the catalyst particles and the inert gas, and then discharges the inert gas to the outside and injects the catalyst particles back into the first reactor 10. In this case, the first reactor 10 may be replenished with a new catalyst through a catalyst discharge pipe when necessary.

According to the exemplary embodiments described above, a system for preventing a catalyst from overheating, which can produce product gas and control heat of a catalyst simultaneously by using the first and second reactors of a simple fluidized bed type as a reactor to produce product gas from reaction gas and a heat exchanging fluidized bed reactor for heat exchange, respectively, can be implemented.

While exemplary embodiments have been particularly shown and described above, it will be understood by those of ordinary skill in the art that various changes in form and details may be made therein without departing from the spirit and scope of the present invention as defined by the following claims.

What is claimed is:

1. A system for preventing a catalyst from overheating, the system comprising:
   a first reactor filled with a catalyst at least in part and configured to receive reaction gas and produce product gas; and
   a second reactor at least partially filled with a catalyst discharged from the first reactor and configured to cool the catalyst discharged from the first reactor,
   wherein the catalyst is circulated between the first reactor and the second reactor by injecting the catalyst cooled in the second reactor into the first rector,
   wherein the second reactor comprises:
   a path of a cooling fluid passing through a catalyst bed in the second reactor; and
   a path to allow the reaction gas to pass through the catalyst bed in the second reactor, and
   wherein the reaction gas is pre-heated by heat exchange with the catalyst during passing through the path of the reaction gas and then supplied to the first reactor.

2. The system of claim 1, wherein the catalyst is a catalyst of a particle shape having a diameter ranging from 1 to 9,000 micrometers.

3. The system of claim 1, further comprising a path of another cooling fluid passing through the first reactor, and
   wherein the catalyst in the first reactor is cooled by the another cooling fluid.

4. The system of claim 1, wherein the first reactor is a fluidized bed reactor and the product gas is produced in a state in which the catalyst in the first reactor is fluidized.

\* \* \* \* \*